US012740972B2

(12) United States Patent
Nithiyanandam et al.

(10) Patent No.: US 12,740,972 B2
(45) **Date of Patent: *Sep. 22, 2026**

(54) PHARMACEUTICAL COMPOSITION OF PITOLISANT HYDROCHLORIDE AND THEIR PROCESS FOR THE PREPARATION

(71) Applicant: MSN Laboratories Private Limited, R & D Center, Hyderabad (IN)

(72) Inventors: Ravi Kumar Nithiyanandam, Hyderabad (IN); Siva Prasad Thota, Hyderabad (IN)

(73) Assignee: MSN Laboratories Private Limited, R & D Center, Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 19/461,494

(22) Filed: Jan. 27, 2026

(65) Prior Publication Data

US 2026/0207574 A1 Jul. 23, 2026

Related U.S. Application Data

(63) Continuation of application No. 18/862,530, filed as application No. PCT/IN2023/050427 on May 4, 2023.

(30) Foreign Application Priority Data

May 4, 2022 (IN) ............................ 202241025983
Oct. 1, 2022 (IN) ............................ 202241056548

(51) Int. Cl.
*A61K 31/4453* (2006.01)
*A61K 9/20* (2006.01)

(52) U.S. Cl.
CPC ........ *A61K 31/4453* (2013.01); *A61K 9/2009* (2013.01); *A61K 9/2027* (2013.01); *A61K 9/2054* (2013.01); *A61K 9/2059* (2013.01)

(58) Field of Classification Search
CPC ............. A61K 31/4453; A61K 9/2009; A61K 9/2027; A61K 9/2054
See application file for complete search history.

(56) References Cited

U.S. PATENT DOCUMENTS 7,169,928 B2 1/2007 Schwartz et al.
8,207,197 B2 * 6/2012 Raga ........................ A61P 3/04 514/317
2008/0221162 A1 9/2008 Raga et al.
2022/0402886 A1 12/2022 Venkatragavan et al.

FOREIGN PATENT DOCUMENTS

WO 2021023634 A1 2/2021

OTHER PUBLICATIONS

International Search Report for Application No. PCT/IN2023/050427 mailed Sep. 13, 2023. 3 pgs.

* cited by examiner

*Primary Examiner* — Kamal A Saeed
(74) *Attorney, Agent, or Firm* — Lerner David LLP

(57) ABSTRACT

The present invention relates to a method of manufacturing a pharmaceutical composition containing amorphous pitolisant hydrochloride, including mixing pitolisant free base, hydrochloric acid, and a pharmaceutically acceptable carrier to convert the pitolisant free base into the amorphous pitolisant hydrochloride in-situ.

14 Claims, No Drawings

PHARMACEUTICAL COMPOSITION OF PITOLISANT HYDROCHLORIDE AND THEIR PROCESS FOR THE PREPARATION

CROSS REFERENCE TO RELATED APPLICATIONS

This application is a continuation of U.S. application Ser. No. 18/862,530 filed on Nov. 2, 2024, which is a national phase entry under 35 U.S.C. § 371 of International Application No. PCT/IN2023/050427 filed May 4, 2023, which claims priority from Indian patents application Nos. 202241025983 filed on May 4, 2022 and 202241056548 filed on Oct. 1, 2022, all of which are incorporated herein by reference.

FIELD OF THE INVENTION

The present invention relates to a pharmaceutical compositions, that comprise amorphous form of pitolisant or pharmaceutically acceptable salts thereof, which is efficacious, chemically stable and physiologically balanced for safety and efficacy. The said invention is used for treatment of excessive daytime sleepiness (EDS) and cataplexy in adult patients with narcolepsy. Further the invention relates to the process for the preparation of said pharmaceutical composition.

BACKGROUND OF THE INVENTION

Narcolepsy is a rare and disabling disorder affecting the sleep and wakefulness regulation. A deficit of hypocretin (orexin), a wake stimulating peptide produced by thalamic nuclei, is hypothesized to be the key underlying mechanism. The two cardinal clinical features of narcolepsy are excessive daytime sleepiness (EDS) and cataplexy. It is a chronic and often extremely incapacitating disease with negative impact on the quality of life of affected patients, interfering with every aspect of life, in work and social settings. The prevalence of narcolepsy with cataplexy is estimated to be between 25 and 50 per 100,000 people.

Treatment strategies rely on relief of symptoms. With EDS being the most prevalent and the most problematic for the patients, most of the treatments target this particular symptom. Stimulant medications, by increasing monoaminergic activity, have been the milestone of therapy for many decades. Modafinil is approved for the treatment of excessive sleepiness related to narcolepsy, but its mechanism of action is not fully understood. It is considered as the first line pharmacological treatment for EDS, but there is discrepancy on its effect on cataplexy. Amphetamines and methylphenidate, acting on dopamine and norepinephrine receptors, have been commonly used in this indication. However, these medications can have serious side effects, mostly on cardiovascular and nervous systems (hypertension, tachycardia, anxiety, depression, mania, motor tics, etc.) and could lead to abuse disorders and weight loss. Cataplexy is treated by sodium oxybate and antidepressants. Sodium oxybate is also approved for the treatment of EDS in narcolepsy but it is associated with significant abuse, dependence and withdrawal symptoms.

Histaminergic neurons are mainly located in the posterior hypothalamus. They play a role in arousal mechanisms. It has been shown that histamine H3 receptors (H3R), only activated by inverse agonists, were able to promote activation of cerebral histamine neurons.

Pitolisant is an orally active antagonist/inverse agonist of the human histamine H3 receptor. It works by enhancing the histaminergic transmissions in brain, acetylcholine release in prefrontal cortex and hippocampus and dopamine release in prefrontal cortex but not in striatum.

The chemical name of pitolisant hydrochloride is 1-{3-[3-(4-chlorophenyl) propoxy] propyl} piperidine, hydrochloride and has the following structure:

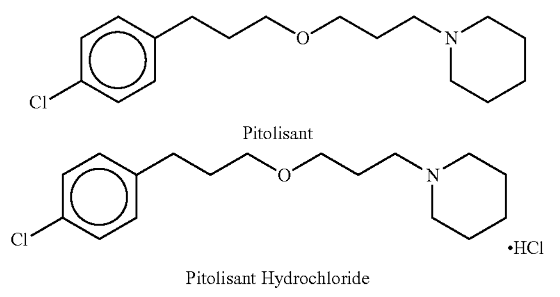

Pitolisant

Pitolisant Hydrochloride

The molecular formula of the pitolisant free base is $C_{17}H_{26}ClNO$ and its molecular weight is 295.85. The molecular formula of the pitolisant hydrochloride is $C_{17}H_{26}ClNO{\cdot}HCl$ and a molecular weight of 332.31. Pitolisant hydrochloride is a white or almost white crystalline powder very soluble in water, ethanol, and methylene chloride, freely soluble in acetone and practically insoluble in cyclohexane. Pitolisant has a non-chiral molecular structure. Therefore, the active substance does not exhibit stereoisomerism.

U.S. Pat. No. 7,169,928 B2 discloses pitolisant and its pharmaceutically acceptable salts, hydrates, or hydrated salts, or their optical isomers, racemates, diastereoisomers or enantiomers.

U.S. Pat. No. 8,207,197 B2 discloses crystalline pitolisant hydrochloride optionally comprising water up to 6%.

Pitolisant was first approved in United States on Aug. 14, 2019 as an immediate release oral tablet dosage form with orphan drug status for EDS in adult patients with narcolepsy and for cataplexy in adult patients with narcolepsy. Initially Bioprojet developed pitolisant, further; Harmony Biosciences acquired the U.S. rights to pitolisant (Wakix) from Bioprojet. Further pitolisant was also approved in EMA on Apr. 4, 2016 as an immediate release oral tablet dosage form with orphan drug status for treatment of narcolepsy. As per EMA the choice of dosage form took into account the following characteristics of the active substance: a fine crystalline powder with good compressibility properties and satisfactory density which is not hygroscopic until 75% RH, is very soluble in water until pH 7.5, is sensitive to excessive oxidative conditions leading to the main identified degradation product, i.e. N-oxide derivative, and has a very strong and prolonged bitter taste.

The amorphous form of pharmacologically active materials has received considerable attention because in theory this form represents the most energetic solid state of a material and thus it should provide the biggest advantage in terms of solubility and bioavailability. The solubility and bioavailability improvements can be attained by using an amorphous form of a drug. Hence inventors of present invention have chosen amorphous form of pitolisant hydrochloride as an active ingredient. However, amorphous form of pitolisant hydrochloride and its pharmaceutical composition are not disclosed in the art.

Hence as a consequence, there is an imperious necessity in the field of pharmaceutical industry to develop stable, more economical & less hazardous reproducible pharmaceutical formulations comprising amorphous form of pitolisant hydrochloride and suitable pharmaceutical carriers or excipients in order to provide required bioavailability to the active substance, stability over shelf life, and bioequivalence with the Innovator.

Further, the inventors of the present invention have developed a novel technique for the preparation of a pharmaceutical composition comprising amorphous form of pitolisant hydrochloride and suitable pharmaceutical carriers or excipients that is relatively stable, and economical.

The inventors of the present invention have chosen granulation technique for the preparation of a pharmaceutical composition comprising amorphous form of pitolisant hydrochloride and suitable pharmaceutical carriers or excipients.

Granulation is the process of a particle enlargement by agglomeration technique, is one of the most significant unit operations in the production of pharmaceutical dosage forms, mostly tablets and capsules. Granulation process transforms fine powders into free-flowing, dust-free granules that are easy to compress. Nevertheless, granulation poses numerous challenges due to high quality requirement of the formed granules. Changes in dissolution profiles are less likely to occur in tablets made by granulation on storage than in those made from other types. This is extremely important because the official compendium now requires dissolution specifications in most solid dosage forms. There are some different granulation techniques can be utilized for preparation of the mix prior to the compression stage: dry granulation, or wet granulation.

Inventors of the present application surprisingly or unexpectedly found a novel technique for the preparation of a pharmaceutical composition comprising amorphous form of pitolisant hydrochloride, wherein the free base of pitolisant is converted into pitolisant hydrochloride by treating the free base of pitolisant with a source of hydrochloric acid in a solvent and mixing the resulting mixture with pharmaceutically acceptable excipients by careful selection of pharmaceutically acceptable carriers/excipients. By this the inventors of the present invention could be able to achieve a pharmaceutical composition comprising amorphous form of pitolisant hydrochloride. Further, it is possible to prepare a stable and fast disintegrating dosage form such as tablets using conventional means, which always provide a further opportunity to improve the drug performance characteristics of such product and has often proved to be successful in improving the solubility, thus dissolution and bioavailability of drugs because it is simple, economic, cost-effective, industrially amenable to scale up and advantageous.

Without being bound by any theory, the inventors of the present invention have developed a solid pharmaceutical composition which exhibits a dissolution profile and bioavailability that is at least comparable to that of known Wakix® formulations, particularly formulations comprising amorphous pitolisant hydrochloride while allowing for substantially less complex and inexpensive preparation.

SUMMARY OF THE INVENTION

The present invention relates to a pharmaceutical composition comprising amorphous form of pitolisant hydrochloride, wherein, said invention is used for treatment of excessive daytime sleepiness (EDS) and cataplexy in adult patients with narcolepsy. Further the invention relates to the process for preparation of said pharmaceutical composition.

First embodiment of the present invention is to provide a pharmaceutical composition comprising amorphous form of pitolisant hydrochloride.

First aspect of first embodiment of the present invention is to provide a pharmaceutical composition comprising amorphous form of pitolisant hydrochloride and one or more pharmaceutically acceptable excipients; wherein said excipients are those which improve the solubility and stability of the said pharmaceutical composition.

Second embodiment of the present invention is to provide a process for preparing pharmaceutical composition comprising amorphous form of pitolisant hydrochloride, wherein the process for the preparation of amorphous form of pitolisant hydrochloride comprises converting pitolisant base into pitolisant hydrochloride by mixing pitolisant with hydrochloric acid in a solvent, mixing the obtained pitolisant hydrochloride solution with the pharmaceutically acceptable carriers/excipients and preparing a pharmaceutical composition comprising amorphous form of pitolisant hydrochloride.

First aspect of the second embodiment of the present invention is to provide a pharmaceutical composition, wherein, said pharmaceutically acceptable carriers/excipients include but not limited to one or more filler, diluent, disintegrants, surfactants, glidants and lubricants etc.

Third embodiment of the present invention is to provide a process for preparing a pharmaceutical composition comprising amorphous form of pitolisant hydrochloride, wherein said process for the preparation of pharmaceutical composition comprises granulation technique.

First aspect of the third embodiment of the present invention, wherein, said granulation technique preferably comprises wet granulation.

Fourth embodiment of the present invention is to provide a pharmaceutical composition comprising amorphous form of pitolisant hydrochloride, and one or more pharmaceutically acceptable excipients; wherein amorphous form of pitolisant hydrochloride is present in the composition is from about 1 mg to about 40 mg with respect to total weight of the composition.

Fifth embodiment of the present invention discloses methods to access to pharmaceutical formulations of amorphous pitolisant hydrochloride for use as medicament for the treatment of excessive daytime sleepiness (EDS) and cataplexy in adult patients with narcolepsy.

The present invention may be embodied in other specific form with out departing its spirit or essential characteristics. The described embodiments are to be considered in all respect only as illustrative and not restrictive. The scope of invention is, therefore, indicated by the appended claims rather than by the foregoing description. All changes which come within the meaning and range of equivalency of the claims are to be embraced within the scope.

DETAILED DESCRIPTION OF THE INVENTION

The present invention relates to pharmaceutical composition comprising amorphous form of pitolisant hydrochloride, wherein, said invention is used for treatment of excessive daytime sleepiness (EDS) and cataplexy in adult patients with narcolepsy. Further the invention relates to the process for preparation of said pharmaceutical composition.

This disclosure is not limited to the particular systems, devices and methods described, as these may vary. The terminology used in the description is for the purpose of describing the particular versions or embodiments only, and is not intended to limit the scope.

The term "active ingredient", "drug", "biologically active molecule", "biologically active moiety" or "biologically active agent", when used herein means any substance which can affect any physical or biochemical properties of a biological organism, including but not limited to viruses, bacteria, fungi, plants, animals, and humans. In particular, as used herein, Active ingredient include any substance intended for diagnosis, cure, mitigation, treatment, or prevention of disease in humans or other animals, or to otherwise enhance physical or mental well-being of humans or animals or to have direct effect in restoring, correcting or modifying physiological functions in human beings. As used herein includes human histamine H3 receptor antagonist/partial agonist or a pharmaceutically acceptable salt thereof, preferably, a Pitolisant hydrochloride.

As used herein, the term "composition or pharmaceutical composition or formulation" refers to solid dosage forms, such as but not limited to tablet, capsule, granules, pellets, films, implants, suppositories etc., Preferably, the pharmaceutical composition is an oral dosage form, more preferably tablet dosage form.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, not with standing that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. The compositions may be administered to a subject to prevent progression of physiological symptoms or to prevent progression of the underlying disorder.

As used herein, the term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

As used herein "Pharmaceutically acceptable carriers" or "pharmaceutically acceptable excipient" or "pharmaceutically acceptable inactive ingredient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

When used here in the term "about" will compensate for variability allowed for in the pharmaceutical industry and inherent in pharmaceutical products, such as differences in product strength due to manufacturing variation and time-induced product degradation. In one embodiment the term allows for any variation which in the practice of pharmaceuticals would allow the product being evaluated to be considered pharmaceutically equivalent or bioequivalent to the recited strength. In another embodiment the term allows for any variation within ±10% of the recited strength or concentration of the formulation.

The invention can be defined based on several principal embodiments which can be combined in any manner physically and mathematically possible to create additional principal embodiments.

First embodiment of the present invention is to provide a pharmaceutical composition comprising amorphous form of pitolisant hydrochloride.

First aspect of first embodiment of the present invention is to provide a pharmaceutical composition comprising amorphous form of pitolisant hydrochloride and one or more pharmaceutically acceptable excipients; wherein said excipients are those which improve the solubility and stability of the said pharmaceutical composition.

Second embodiment of the present invention is to provide a process for preparing a pharmaceutical composition comprising amorphous form of pitolisant hydrochloride, wherein the process for the preparation of amorphous form of pitolisant hydrochloride comprises converting pitolisant base into pitolisant hydrochloride by mixing pitolisant with hydrochloric acid in a solvent, mixing the obtained pitolisant hydrochloride solution with the pharmaceutically acceptable carriers/excipients and preparing a pharmaceutical composition comprising amorphous form of pitolisant hydrochloride.

First aspect of the second embodiment of the present invention is to provide a pharmaceutical composition, wherein, said pharmaceutically acceptable carriers/excipients include but not limited to one or more filler, diluent, disintegrants, surfactants, glidants and lubricants etc.

Pharmaceutical excipients are substances other than the pharmacologically active drug or prodrug which are included in the manufacturing process or are contained in a finished pharmaceutical product dosage form. In addition to transporting the active drug to the site in the body where the drug is intended to exert its action, excipients play an important part in the manufacturing process. They may also be important for keeping the drug from being released too early in the assimilation process in places where it could damage tender tissue and create gastric irritation or stomach upset. Some helps the drug to disintegrate into particles small enough to reach the blood stream more quickly and still others protect the product's stability so it will be at maximum effectiveness at time of use. In addition, some excipients are used to aid the identification of a drug product.

Last, but not the least, some excipients are used simply to make the product taste and look better. This improves patient compliance. Although technically "inactive" from a therapeutic sense, pharmaceutical excipients are critical and essential components of a modern drug product. In many products, excipients make up the bulk of the total dosage form. Apart from the drug's active ingredient, other essential components include diluents or fillers, binders, disintegrants, glidant, lubricants, coloring agents and preservatives.

The pharmaceutical composition according to the invention typically comprises at least one diluent/adsorbents.

Suitable diluents/adsorbents include monosaccharides and oligosaccharides such as glucose, fructose, saccharose, lactose (anhydrous and monohydrate), raffinose, trehalose and dextrates, sugar alcohols such as mannitol, sorbitol, maltitol, xylitol and lactitol, compressible sugar, microcrystalline cellulose, magnesium aluminium metasilicate, pregelatinized starch, corn/maize starch, powdered cellulose, silicified microcrystalline cellulose, silicon dioxide, crospovidone, croscarmellose sodium, calcium hydrogen phosphate, calcium carbonate, calcium lactate and mixtures thereof. The diluents/adsorbents are used interchangeably in the present invention. The preferred diluent/adsorbent is at least one selected from silicified microcrystalline cellulose, microcrystalline cellulose, magnesium aluminium metasilicate.

The binder is used in a pharmaceutical composition to improve the flow properties of powder and to improve compatibility. The binders are selected from but are not limited to cellulose derivatives such as hydroxypropylcellulose, hydroxyethylcellulose, methylcellulose, carboxymethylcellulose sodium, microcrystalline cellulose, gelatin, starch paste, pregelatinized starch, povidone or polyvinylpyrrolidone and sucrose.

Disintegrating agents suitable for use in the present formulations include which facilitate the break up of a tablet when it is placed in aqueous environment. Disintegrants once in contact with water or gastric juice, swell, hydrate, change in volume or form to produce a disruptive force that opposes the efficiency of the binder/s causing the compressed table to break apart. The disintegrants are selected from maize starch, potato starch, carboxymethylstarche, sodium starch glycolate, crospovidones, sodium carboxymethylcelluloses, sodium alginate, microcrystalline cellulose, methacrylic acid copolymer, potassium polacrilin. The most preferred disintegrant in a present pharmaceutical composition are crospovidone.

Glidant in the context of the present invention is taken to mean an ingredient which enhances product flow by reducing inter-particulate friction. The glidant is selected from colloidal silicon dioxide, aluminum silicate, magnesium silicate, calcium stearate, fumed silica, talc, powdered cellulose, starch and tribasic calcium phosphate. The most preferred glidant are talc and colloidal silicon dioxide.

Lubricants are used in the tablet formulation to reduce the friction during the compression stages and to prevent the sticking of the tablet to the punch faces. Lubricant is selected from stearic acid (calcium stearate and magnesium stearate), vegetable oils (corn oil), mineral oils, polyethylene glycol, inorganic salts (such as sodium chloride), organic salts (sodium benzoate, sodium acetate), and polyvinyl alcohols. The most preferred lubricant is magnesium stearate.

Coating is a process by which an essentially dry, outer layer of coating material is applied to the surface of a dosage form in order to confer specific benefits over uncoated variety. Coating may be carried out by using coating agents such as Opadry Yellow, Opadry Black, Opadry Red and Opadry White.

Third embodiment of the present invention is to provide a process for pharmaceutical composition comprising amorphous form of pitolisant hydrochloride, wherein said process comprises granulation technique.

First aspect of the third embodiment of the present invention, wherein, said granulation technique preferably comprises wet granulation.

Fourth embodiment of the present invention is to provide a pharmaceutical composition comprising amorphous form of pitolisant hydrochloride, and one or more pharmaceutically acceptable excipients; wherein pitolisant hydrochloride is present in the composition is from about 1 mg to about 40 mg with respect to total weight of the composition.

Fifth embodiment of the present invention discloses methods to access to pharmaceutical formulations of amorphous pitolisant hydrochloride for use as medicament for the treatment of excessive daytime sleepiness (EDS) and cataplexy in adult patients with narcolepsy.

In an aspect of the present invention the pharmaceutical composition here in can be characterized by X-ray powder diffraction technique to confirm whether pitolisant hydrochloride active substance present in composition is in amorphous form or not.

The said X-ray powder diffraction analysis can be carried out by using BRUKER/D8 ADVANCE X-Ray diffractometer using CuKα radiation of wavelength 1.5406 A° and at a continuous scan speed of 0.03°/min.

The use of the terms "a," "an" and "the" and similar references in the context of this disclosure (especially in the context of the following) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the invention. No language in the specification should be construed as indicating any non-claimed element as essential to the practice of the present disclosure.

EXAMPLES

Example 1, 2, 3 & 4

| S. No. | Name of the Raw material | Ex. 1 | Ex. 2 | Ex. 3 | Ex. 4 |
|---|---|---|---|---|---|
| | | 17.8 mg//Tablet | | | |
| | **Intragranular** | | | | |
| 1 | Pitolisant | 17.800 | 17.800 | 17.800 | 17.800 |
| 2 | Silicified Microcrystalline Cellulose | 123.200 | 132.200 | 123.200 | *** |
| 3 | Microcrystalline Cellulose | *** | *** | *** | 102.200 |
| 4 | Crospovidone | 20.000 | *** | *** | 20.000 |
| 5 | Croscarmellose sodium | *** | 15.000 | 30.000 | *** |
| | **Granulating Solvent** | | | | |
| 6 | Aqueous Hydrochloric acid (37%) | 2.207 | 2.207 | 3.000 | 2.500 |
| 7 | Purified Water | 40.000 | 40.000 | 40.000 | 25.000 |
| | **Extra granular** | | | | |
| 8 | Crospovidone | 10.000 | *** | *** | *** |
| 9 | Croscarmellose sodium | *** | 10.000 | *** | *** |
| 10 | Colloidal silicon dioxide | 1.000 | *** | 1.000 | 2.000 |
| 11 | Magnesium Stearate | 3.000 | 5.000 | 3.000 | 3.000 |
| 12 | Talc | 5.000 | *** | 5.000 | 5.000 |
| | Core Tablet weight | 180.000 | 180.000 | 180.000 | 150.000 |
| | **Film Coating** | | | | |
| 13 | Opadry White 85F580031 | 5.400 | 5.400 | 5.400 | *** |
| 14 | Opadry White 03O18646 | *** | *** | *** | 4.500 |
| | Total Tablet weight | 185.400 | 185.400 | 185.400 | 154.500 |

Manufacturing Process for 1, 2, 3, & 4:

Step 1: Sifted the required quantity of silicified microcrystalline cellulose/microcrystalline cellulose, croscarmellose sodium/crospovidone through suitable mesh.

Step 2: loaded the above sifted materials into Raid mixer granulator and mix for 10 minutes.

Step 3: added the required quantity of aqueous hydrochloric acid (37%) in purified water under stirring and continued the stirring until a clear solution was obtained.

Step 4: added the required quantity of Pitolisant free base to the above step 3 solution under stirring and continued the stirring until a clear solution was obtained.

Step 5: added the drug solution obtained from step 4 to dry mix powder of step 2, Step 6: dried the wet mass in fluid bed dryer, Step 7: sifted the dried granules through suitable mesh and retains are co-milled with 40 G at slow speed, continued this process until all the material was passed through suitable mesh Step 8: sifted the extra granular material of crospovidone/croscarmellose sodium through suitable mesh and blended with milled granules obtained from step 7 in blender for 10 min.

Step 9: sifted the extra granular material of colloidal silicon dioxide, talc and magnesium stearate through suitable mesh and blended with the material obtained from step 8 for 5 min.

Tablet Compression: Compressed the blend obtained from step 9 using suitable tooling Preparation of Film Coating Suspension:

Step 10: Taken the purified water in SS 316 container and fixed the stirrer and started stirring to form a vortex. Added the opadry white coating powder in to the vortex slowly to avoid any lump formation. Completed the addition within 5-10 minutes under stirring, and continued the stirring for 45 minutes.

Step 11: coated the tablets until 3.0%+0.5% (2.5-3.5%) weight gain was achieved to the average weight of uncoated tablets.

Example 5, 6, 7 & 8

| S. No. | Name of the Raw material | Ex. 5 | Ex. 6 | Ex. 7 | Ex. 8 |
|---|---|---|---|---|---|
| | | | 17.8 mg//Tablet | | |
| | Intragranular | | | | |
| 1 | Magnesium Aluminium MetaSilicate | 30.000 | 30.000 | 30.000 | 30.000 |
| | Granulating Solvent (API Solution) | | | | |
| 2 | Aqueous Hydrochloric acid (36.5%) | 2.207 | 2.207 | 2.207 | 2.207 |
| 3 | Ethanol | Q.S | Q.S | Q.S | Q.S |
| 4 | Pitolisant | 17.800 | 17.800 | 17.800 | 17.800 |
| | Extra granular | | | | |
| 5 | Silicified Microcrystalline Cellulose | 100.000 | 100.000 | 100.000 | 130.000 |
| 6 | Microcrystalline Cellulose | 28.993 | 8.993 | 38.993 | 8.993 |
| 7 | Crospovidone | 10.000 | 30.000 | *** | *** |
| 8 | Talc | 5.000 | 5.000 | 5.000 | 5.000 |
| 9 | Colloidal Silicon dioxide | 1.000 | 1.000 | 1.000 | 1.000 |
| 10 | Magnesium stearte | 5.000 | 5.000 | 5.000 | 5.000 |
| | Core Tablet weight | 200.000 | 200.000 | 200.000 | 200.000 |
| | Film Coating | | | | |
| 11 | Opadry II White 85F184222 | 6.000 | 6.000 | 6.000 | 6.000 |
| 12 | Purified water | Q.S | Q.S | Q.S | Q.S |
| | Total Tablet weight | 206.000 | 206.000 | 206.000 | 206.000 |

Manufacturing Process for 5, 6, 7 & 8:

Step 1: Sifted the required quantity of magnesium aluminium monosilicate through suitable mesh, Step 2: loaded the above sifted materials into Rapid mixer granulator and dry mix for 10 minutes with impeller slow, Step 3: added the required quantity of aqueous hydrochloric acid (37%) in required quantity of ethanol under stirring and continued the stirring until a clear solution was obtained, Step 4: added the required quantity of Pitolisant free base to the above step 3 solution under stirring and continued the stirring until a clear solution was obtained, Step 5: added the drug solution obtained from step 4 to dry powder of step 2, Step 6: dried the wet mass in fluid bed dryer/vacuum tray drier, Step 7: sifted the dried granules through suitable mesh and retains are co-milled with 40 G at slow speed, continued this process until all the material was passed through suitable mesh, Step 8: sifted the extra granular material silicified microcrystalline cellulose, micro crystalline cellulose, crospovidone, talc, colloidal silicon dioxide, and magnesium stearate through suitable mesh and blended with milled granules obtained from step 7 in blender for 10 min.

Tablet Compression: Compressed the blend obtained from step 8 using suitable tooling Preparation of Film Coating Suspension:

Step 09: Taken the purified water in SS 316 container and fixed the stirrer and started stirring to form a vortex. Added the opadry white coating powder in to the vortex slowly to avoid any lump formation. Completed the addition within 5-10 minutes under stirring, and continued the stirring for 45 minutes.

Step 10: coated the tablets until 3.0%+0.5% (2.5-3.5%) weight gain was achieved to the average weight of uncoated tablets.

The invention claimed is:

1. A method of manufacturing a pharmaceutical composition comprising amorphous pitolisant hydrochloride, comprising:

mixing pitolisant free base, hydrochloric acid, and a pharmaceutically acceptable carrier to convert the pitolisant free base into the amorphous pitolisant hydrochloride in-situ.

2. The method of claim 1, wherein the mixing comprises combining the pitolisant free base and the hydrochloric acid to form a mixture, and adding the pharmaceutically acceptable carrier to the mixture.

3. The method of claim 1, wherein the mixing comprises combining the hydrochloric acid and the pharmaceutically acceptable carrier to form a mixture, and adding the pitolisant free base to the mixture.

4. The method of claim 1, wherein the mixing is performed in a granulator.

5. The method of claim 1, wherein the pharmaceutically acceptable carrier comprises at least one of a diluent or a disintegrant, wherein the diluent comprises one or more of silicified microcrystalline cellulose, microcrystalline cellulose, or magnesium aluminium metasilicate, and wherein the disintegrant comprises one or more of crospovidone, croscarmellose sodium, or sodium starch glycolate.

6. The method of claim 1, wherein the hydrochloric acid is in a solvent.

7. The method of claim 6, wherein the solvent is at least one of water or ethanol.

8. The method of claim 2, wherein the hydrochloric acid is in a solvent.

9. The method of claim 8, wherein the solvent is at least one of water or ethanol.

10. The method of claim 3, wherein the hydrochloric acid is in a solvent.

11. The method of claim 10, wherein the solvent is at least one of water or ethanol.

12. The method of claim 1, further comprising forming the pharmaceutical composition.

13. The method of claim 12, wherein the forming comprises a step of granulation.

14. The method of claim 13, wherein the granulation is performed by at least one of dry granulation or wet granulation.

* * * * *